United States Patent
Sigl et al.

(10) Patent No.: US 7,714,179 B2
(45) Date of Patent: May 11, 2010

(54) METHOD FOR THE PRODUCTION OF $C_5$ ALDEHYDES AND PROPENE FROM A $C_4$ STREAM CONTAINING 1-BUTENE AND 2-BUTENE

(75) Inventors: Marcus Sigl, Mannheim (DE); Markus Schubert, Ludwigshafen (DE); Jürgen Stephan, Mannheim (DE); Rainer Papp, Speyer (DE); Frank Poplow, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 601 days.

(21) Appl. No.: 11/661,543

(22) PCT Filed: Aug. 6, 2005

(86) PCT No.: PCT/EP2005/008561
§ 371 (c)(1),
(2), (4) Date: Feb. 27, 2007

(87) PCT Pub. No.: WO2006/024366
PCT Pub. Date: Mar. 9, 2006

(65) Prior Publication Data
US 2008/0033223 A1    Feb. 7, 2008

(30) Foreign Application Priority Data
Aug. 27, 2004  (DE) .................... 10 2004 041 850

(51) Int. Cl.
*C07C 6/00*    (2006.01)
*C07C 45/49*   (2006.01)

(52) U.S. Cl. .................. 585/328; 585/324; 585/643; 568/429

(58) Field of Classification Search ............... 585/328, 585/324, 643; 568/429
See application file for complete search history.

(56) References Cited

U.S. PATENT DOCUMENTS

| | | |
|---|---|---|
| 5,877,365 A | 3/1999 | Chodorge et al. |
| 5,898,091 A | 4/1999 | Chodorge et al. |
| 2003/0153791 A1 | 8/2003 | Richter et al. |
| 2004/0138512 A1 | 7/2004 | Roper et al. |

FOREIGN PATENT DOCUMENTS

| | | |
|---|---|---|
| DE | 101 18 634 | 10/2002 |
| DE | 10 2004 009 803 | 9/2005 |
| DE | 10 2004 009 804 | 9/2005 |
| DE | 10 2004 009 805 | 9/2005 |
| EP | 0 742 195 | 11/1996 |
| EP | 0 742 234 | 11/1996 |
| WO | WO-2005/009934 | 2/2005 |

*Primary Examiner*—Thuan Dinh Dang
(74) *Attorney, Agent, or Firm*—Connolly Bove Lodge & Hutz LLP

(57) ABSTRACT

Processes for preparing a $C_5$ aldehyde and propene are disclosed, the processes comprising: (a) providing a feedstream, the feedstream comprising butane, 1-butene, 2-butene and 1,3-butadiene, the 1,3-butadiene present in the feedstream in an amount up to 1000 ppm; (b) contacting the feedstream with hydrogen and carbon monoxide in the presence of a hydroformylation catalyst to form a 2-butene-rich butane stream and a $C_5$ aldehyde; (c) separating the 2-butene-rich butane stream and the $C_5$ aldehyde; and (d) contacting the 2-butene-rich butane stream with ethene in the presence of a metathesis catalyst to form a propene-containing hydrocarbon stream.

20 Claims, 2 Drawing Sheets

METHOD FOR THE PRODUCTION OF $C_5$ ALDEHYDES AND PROPENE FROM A $C_4$ STREAM CONTAINING 1-BUTENE AND 2-BUTENE

CROSS-REFERENCE TO RELATED APPLICATIONS

This application is a national stage application, under 35 U.S.C. 371, of PCT/EP2005/008561 filed Aug. 6, 2005, which claims benefit of German Application No. 10 2004 041 850.0 filed Aug. 27, 2004.

BACKGROUND OF THE INVENTION

For the economic utilization of $C_4$ streams, as can be obtained, for example, from cracking processes or by dehydrogenating butanes, various processes are already known. These starting streams typically comprise relatively large amounts of 1,3-butadiene, 1-butene and 2-butenes. In addition, significant proportions of butanes, and also isobutene in the case of cracking processes, are often present. In order to achieve a very economically viable process, the individual components each have to be converted to salable products of maximum value, without the other components being impaired thereby. Particularly advantageous in this context is also the complete or partial conversion of one $C_4$ component to another $C_4$ component which is fed to an economically more attractive use. To this end, generally complex, multi-stage processes are required, in which the individual $C_4$ components are processed stepwise. Such processes are described, for example, in DE-A-10118634, EP-A-742 195 and 742 234.

Pure 1,3-butadiene constitutes a sought-after monomer. Pure 1-butene is likewise a high-cost monomer, but after hydroformylation to valeraldehyde and subsequent aldol condensation and hydrogenation to propylheptanol also finds an economically significant outlet as a plasticizer component and surfactant alcohol. Isobutene serves as a starting material for fuel and lubricant additives after polymerization to polyisobutene, as a fuel additive after etherification with methanol to MTBE, and as knock-resistant gasoline alkylate after dimerization to diisobutene and subsequent hydrogenation. In contrast, the direct chemical reaction of 2-butenes is hitherto industrially insignificant. Here, an olefin metathesis with ethene, which converts 2-butenes to the valuable olefin monomer propene, is viable.

BRIEF SUMMARY OF THE INVENTION

The present invention relates to a process for preparing $C_5$ aldehydes and propene from a 1-butene- and 2-butene-containing $C_4$ stream.

It is an object of the present invention to develop a process which enables a substantially full and highly economically viable utilization of a $C_4$ stream to prepare propene and $C_5$ aldehydes.

Accordingly, a process has been found for preparing $C_5$ aldehydes and propene from a 1-butene- and 2-butenes-containing $C_4$ stream which contains up to 1000 ppm by weight of 1,3-butadiene ($C_4$ starting stream), comprising a) a hydroformylation stage in which the $C_4$ starting stream is contacted in the presence of a customary hydroformylation catalyst with hydrogen and carbon monoxide, and the thus formed $C_5$ aldehydes and the thus formed 2-butene-rich $C_4$ stream are subsequently separated from one another, and b) a metathesis stage in which the 2-butene-rich $C_4$ stream formed in the hydroformylation stage is contacted with ethene in the presence of a customary metathesis catalyst and the propene is removed from the thus formed propene-containing hydrocarbon stream.

Suitable $C_4$-containing streams are in particular raffinates (raffinate I or II). Such raffinates I can be prepared by 3 different methods:

In the first method, the $C_4$ starting stream is provided by

Ia) in step Ia, subjecting naphtha or other hydrocarbon compounds to a steamcracking or FCC process and drawing off from the thus formed stream a $C_4$ olefin mixture which comprises 1-butene, 2-butene and more than 1000 ppm by weight of butadienes, with or without butynes and isobutene, and IIa) preparing from the $C_4$ olefin mixture formed in step Ia a $C_4$ hydrocarbon stream consisting substantially of 1-butene and 2-butenes, with or without butanes and isobutene (raffinate 1), by hydrogenating the butadienes and butynes to butenes or butanes by means of selective hydrogenation, or removing the butadienes and butynes by extractive distillation to such an extent that the content of 1,3-butadiene is not more than 1000 ppm by weight.

In the second method, the $C_4$ starting stream is provided by

Ib) in step Ib, preparing from a hydrocarbon stream comprising butanes, by dehydrogenation and subsequent purification, a $C_4$ olefin mixture which comprises isobutene, 1-butene, 2-butene and more than 1000 ppm by weight of butadienes, with or without butynes and butanes, IIb) preparing from the $C_4$ olefin mixture formed in step Ib a $C_4$ hydrocarbon stream consisting substantially of isobutene, 1-butene and 2-butenes, with or without butanes (raffinate 1), by hydrogenating the butadienes and butynes to butenes or butanes by means of selective hydrogenation, or removing the butadienes and butynes by extractive distillation to such an extent that the content of 1,3-butadiene is not more than 1000 ppm by weight.

In the third method, the $C_4$ starting stream (in the form of raffinate II) is provided by Ic) preparing from methanol by dehydrogenation a $C_4$ olefin mixture (MTO process) which comprises isobutene, 1-butene and 2-butene, with or without butadienes, alkynes and butanes, and Ic) freeing the $C_4$ olefin mixture of butadienes or alkynes by distillation, selective hydrogenation or extractive distillation.

BRIEF DESCRIPTION OF THE SEVERAL VIEWS OF THE DRAWING

The foregoing summary, as well as the following detailed description of the invention, may be better understood when read in conjunction with the appended drawings. For the purpose of assisting in the explanation of the invention, there are shown in the drawings representative embodiments which are considered illustrative. It should be understood, however, that the invention is not limited in any manner to the precise arrangements and instrumentalities shown. In the drawings.

DETAILED DESCRIPTION OF THE INVENTION

Figure 1:
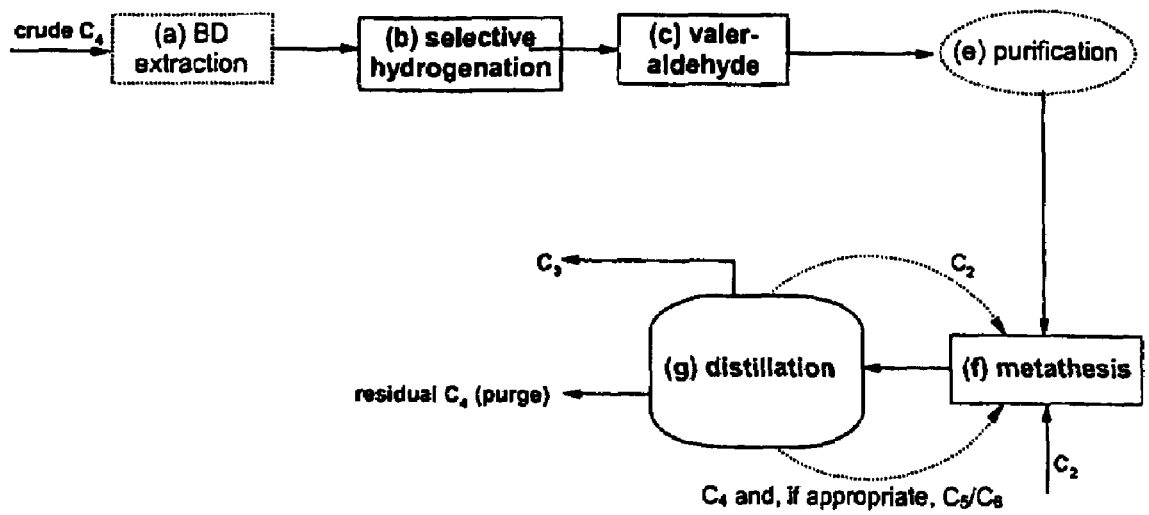
FIG. 1 is a schematic process diagram in accordance with an embodiment of the present invention.
Figure 2:
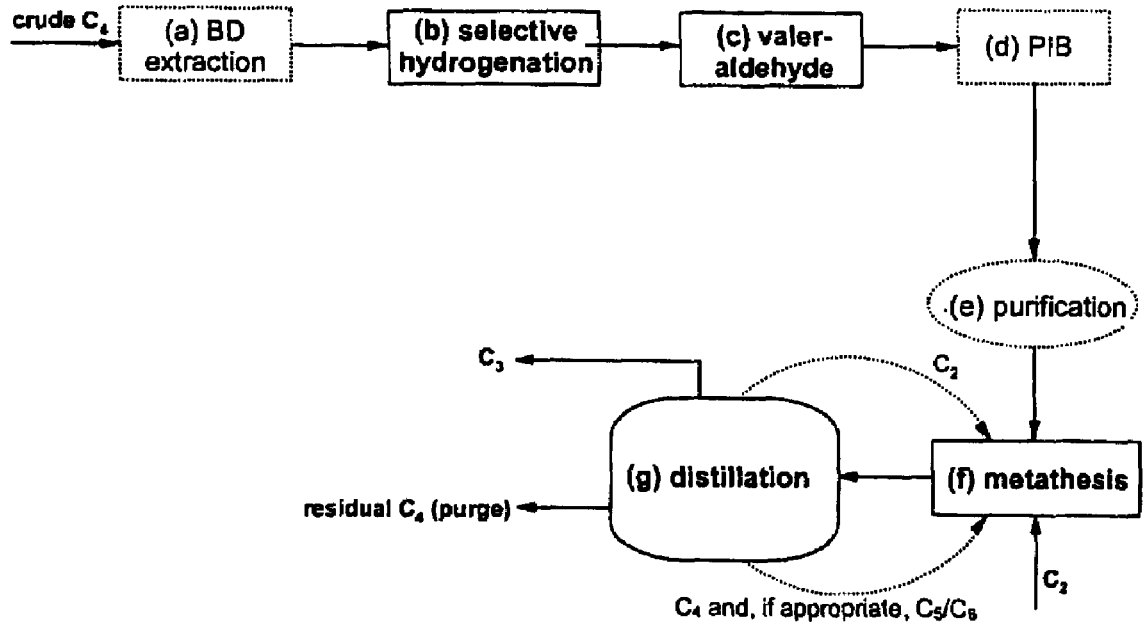
FIG. 2 is a schematic process diagram in accordance with an embodiment of the present invention.
Figure 3:
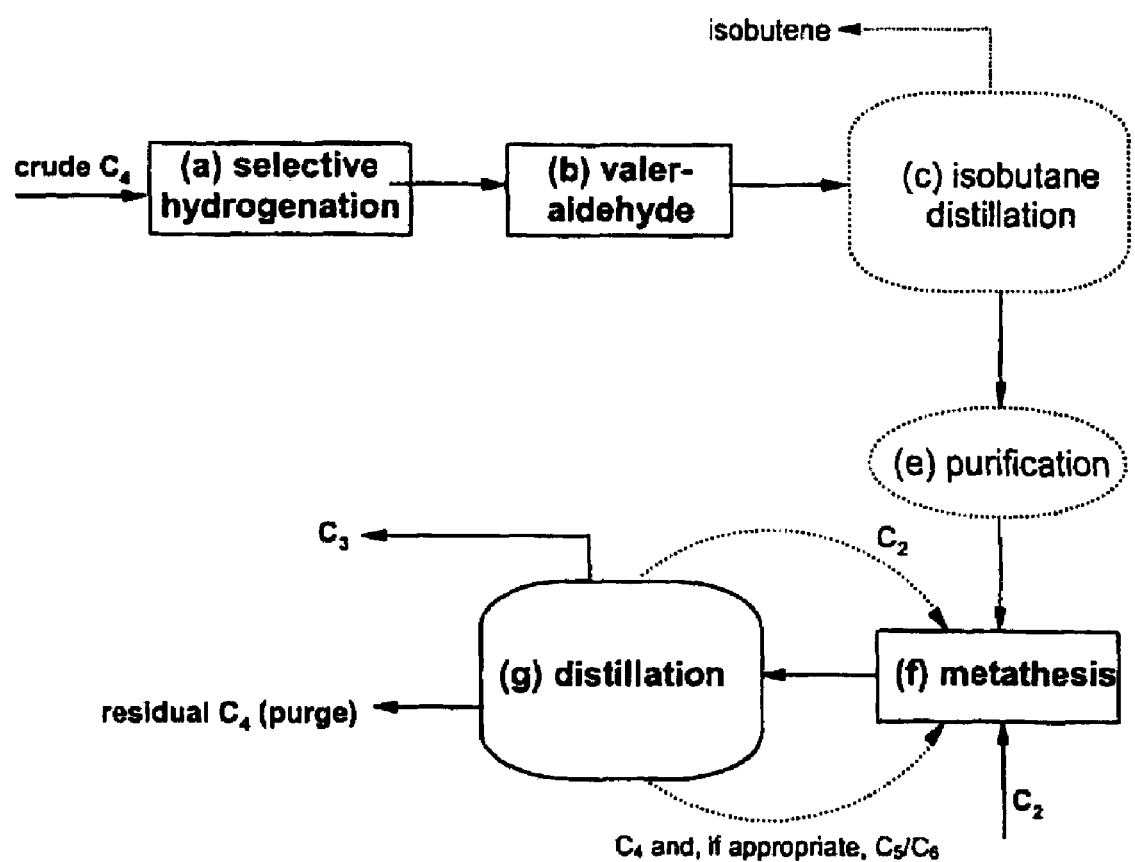
FIG. 3 is a schematic process diagram in accordance with an embodiment of the present invention.

Raffinate II has substantially the same composition as raffinate I, except for the fact that raffinate II comprises smaller amounts of isobutene. Typically, raffinate II has amounts of less than 10% by weight, preferably less than 5% by weight, of isobutene.

Raffinate II can be prepared from raffinate I by removing from raffinate I the substantial proportion of the isobutene by known chemical, physicochemical or physical methods.

For this purpose, there are in principle three fundamentally different possibilities: a) a distillative removal, b) a removal by etherification/extraction and c) direct polymerization to polyisobutene.

The distillation (method a) takes place in an apparatus suitable therefor, for example a bubble-cap tray column, column having random packing, column having structured packing or dividing wall column. The distillation column is preferably configured with from 20 to 80 theoretical plates. The reflux ratio is generally from 5 to 50. The distillation is generally carried out at a pressure of from 5 to 20 bar.

Owing to the low boiling point of isobutene and 1-butene in comparison to 2-butenes and n-butane, the top stream comprises mainly isobutene and 1-butene, the bottom stream mainly 2-butenes and n-butane. The content of low boilers (isobutene and 1-butene) in the bottom stream is less than 40%, preferably less than 30% and more preferably 5-20%. The content of high boilers (2-butenes and n-butane) in the top stream is less than 40%, preferably less than 30% and more preferably from 5 to 20%.

In method b), the procedure is typically to contact raffinate I with an alkyl alcohol, preferably a $C_1$- to $C_4$-alkyl alcohol, and a customary catalyst for the formation of alkyl tert-butyl ether, and to remove the alkyl tert-butyl ether formed from the remaining raffinate II. Particularly preferred alcohols: MeOH, BuOH.

The etherification is effected preferably in the presence of an acidic ion exchanger in a three-stage reactor battery, in which flooded fixed bed catalysts are flowed through from top to bottom, at a reactor inlet temperature of from 0 to 60° C., preferably from 10 to 50° C., an outlet temperature of from 25 to 85° C., preferably from 35 to 75° C., a pressure of from 2 to 50 bar, preferably from 3 to 20 bar, and a ratio of alcohol to isobutene of from 0.8 to 2.0, preferably from 1.0 to 1.5.

In method c), the procedure is typically to contact raffinate I with a customary catalyst for the polymerization of isobutene and to remove the polyisobutylene formed from the remaining $C_4$ starting stream. The catalyst used is preferably a homogeneous or heterogeneous catalyst from the class of the Brønsted or Lewis acids. The catalyst is preferably boron trifluoride.

If it improves economic viability of the overall process, optionally removed isobutene may also be fed to a skeletal isomerization—a combination of distillation and skeletal isomerization in a type of reactive distillation is also possible at this point—in order to increase the amounts of linear olefins and thus to increase the yields in the 1-butene-utilizing stage or the metathesis.

Preference is given to carrying out the extractive distillation in step IIa, IIb or IIc with a butadiene-selective solvent selected from the class of polar aprotic solvents such as acetone, furfural, acetonitrile, dimethylacetamide, dimethylformamide and N-methylpyrrolidone.

The selective hydrogenation in step IIa, IIb or IIc may be used for a substantial reduction of diolefins or acetylenic compounds, since these compounds would impair the downstream process stages. In addition, the selective hydrogenation of a major amount of 1,3-butadiene can also considerably increase the amount of linear monoolefins, which increases the production capacity of downstream stages. Suitable catalysts and methods (for example $H_2$ supply) allow the 1-butene to 2-butene ratio in the selective hydrogenation to be controlled within certain limits (known as hydroisomerization). Since there are particularly attractive economic means of utilization, especially for the 1-butene, 1-butene to 2-butene ratios of at least 1:3, preferably of at least 2:3, more preferably of more than 1:1, are sought after. Preference is given to carrying out the partial step of selective hydrogenation in the liquid phase over a metal selected from the group of nickel, palladium and platinum, on a support, preferably palladium on alumina, at a temperature of from 20 to 200° C., a pressure of from 1 to 50 bar, a volume flow rate of from 0.5 to 30 $m^3$ of fresh feed per $m^3$ of catalyst per hour and a ratio of recycle to feed stream of from 0 to 30 with a molar ratio of hydrogen to diolefins of from 0.5 to 50.

When the content of 1,3-butadiene in the $C_4$ olefin mixture obtained in step Ia or step Ib is 5% by weight or more, the content of 1,3-butadiene is typically lowered by means of extractive distillation to a content between 1000 ppm by weight and 5% by weight, and the content of 1,3-butadiene is subsequently lowered further by means of selective hydrogenation to 1000 ppm by weight or less.

The $C_4$ starting stream preferably has a ratio of 1-butene to 2-butenes of from 3:1 to 1:3.

The content of 1,3-butadiene is preferably less than 300 ppm by weight, more preferably less than 100 ppm by weight.

In general, the $C_4$ starting stream comprises from 2 to 50% by weight of butanes, from 15 to 80% by weight of 2-butenes and from 20 to 60% by weight of 1-butene, from 20 to 1000 ppm by weight of butadienes and from 0 to 50% of isobutene.

The hydroformylation stage may generally be carried out in the manner customary and known to those skilled in the art. A good review with numerous further references can be found, for example, in M. Beller et al., Journal of Molecular Catalysis A, 104, 1995, pages 17 to 85 or in Ullmann's Encyclopedia of Industrial Chemistry, $6^{th}$ edition, 2000 electronic release, Chapter "ALDEHYDES, ALIPHATIC AND ARALIPHATIC—Saturated Aldehydes". The information given there enables those skilled in the art to hydroformylate both the linear and the branched alkenes.

In the hydroformylation stage, valeraldehyde (n-pentanal) is prepared under transition metal catalysis from 1-butene with addition of synthesis gas ($CO:H_2$ of from 3:1 to 1:3, preferably from 1.5:1 to 1:1.15).

The catalysts used for the hydroformylation reaction are generally rhodium complexes having phosphorus ligands. The phosphorus ligands are typically a mono- or diphosphine, preferably a triarylphosphine, more preferably triphenylphosphine. The hydroformylation is carried out typically at temperatures of from 50 to 150° C., preferably from 70 to 120° C., and pressures of from 5 to 50 bar, preferably from 10 to 30 bar.

After the hydroformylation stage, the $C_4$ stream (also known as "2-butene-rich $C_4$ stream") comprises typically from 3 to 70% by weight of butanes, from 22 to 90% by weight of 2-butenes, from 20 to 1000 ppm by weight of 1,3-butadiene, from 0 to 10% by weight of 1-butene and from 0 to 65% by weight of isobutene.

The ratio of 1-butene to 2-butene in the 2-butene-rich $C_4$ stream is typically from 1:3 to 1:60.

The 2-butene-rich $C_4$ stream comprises preferably less than 300 ppm, more preferably less than 100 ppm, of 1,3-butadiene.

The conversion of the 1-butenes in this process stage is preferably greater than 80%, the absolute 1-butenes content in the 2-butene-rich $C_4$ stream is preferably less than 5%. The ratio of 1-butene to 2-butene in the 2-butene-rich $C_4$ stream is less than 1:3, preferably less than 1:5.

If the isobutene has not already been removed from the $C_4$ starting stream, the isobutene removal may be connected downstream of the hydroformylation stage. This is preferred for variants a and c. Suitable for this purpose are the same methods as described above for the preparation of raffinate I from raffinate II.

For a high yield of propene in the metathesis stage, an additional purification is generally initially also necessary, which depletes traces of oxygenates, and also if appropriate acetylenes and dienes. The contents of oxygenates, for example water, acetone or ethanol, after the purification stage should in total be less than 100 ppm, preferably less than 50 ppm, more preferably less than 10 ppm. The contents of diolefins should be less than 300 ppm, preferably less than 150 ppm, more preferably less than 100 ppm. The purification of the 2-butene-rich $C_4$ stream consists of one or more stages and may also comprise pressure-swing adsorption, but preference is given to at least one adsorptive process. Preference is given to effecting the purification directly before the metathesis, but may also theoretically be fully or partly upstream of other process stages. Optionally, the purification step may also comprise a selective hydrogenation which also removes residual traces of diolefins and acetylene which have not been fully hydrogenated in the first selective hydrogenation stage or might have been newly formed or have accumulated in later process stages. The purification stage preferably comprises at least one adsorber bed based on an alumina or a molecular sieve for removing oxygenates. Particular preference is given to an embodiment in which at least two adsorber beds based on an alumina or molecular sieve are present and each alternate between adsorption and regeneration mode. Preferred adsorbents are a 13× molecular sieve or high-surface area gamma-alumina (for example Selexsorb from Almatis).

The 2-butene-rich $C_4$ stream is finally fed to a metathesis stage in order to convert the 2-butene into the higher-value propylene monomer. To this end, ethylene is added stoichiometrically (based on 2-butene) or ethylene is added in excess. Although any 1-butene or isobutene present in the stream likewise reacts partly to form higher olefins ($C_5$ and $C_6$) these may be discharged or else recycled into the metathesis, so that there is only a small, if any, net conversion.

If the propene-containing hydrocarbon stream formed in the metathesis stage comprises $C_5$ and $C_6$ olefins, they are removed from the propene and typically recycled into the metathesis stage at least to the extent that the molar ratio of the sum of the unrecycled $C_5$ and $C_6$ olefins to propene is not more than 0.2:1.

Unconverted 2-butene and ethylene may also, if appropriate, be recycled into the metathesis stage, since the metathesis reaction is an equilibrium reaction.

For the metathesis, there are in principle two different useful catalyst types: a) rhenium catalysts which are operated at temperatures in the range from 30 to 150° C., preferably in the range from 35 to 110° C., and b) W-containing, Re-free catalysts which are operated in the gas phase at temperatures of from 200 to 600° C., preferably from 220 to 450° C.

The Re catalysts comprise preferably at least 1% by weight of Re in oxidic form on a support which is composed to an extent of at least 75% by weight of a high-surface area alumina, most preferably gamma-alumina. Special preference is given to catalysts which have an Re content of from 5 to 12% by weight and are supported on pure gamma-$Al_2O_3$. To increase the activity, the catalysts may also additionally comprise dopants, for example oxides of Nb, Ta, Zr, Ti, Fe, Mn, Si, Mo, W, phosphate or sulfate. The catalysts preferably have surface areas of at least 100 m²/g and pore volumes of at least 0.3 ml/g. Suitable Re catalysts are described, for example, in DE-A 10 2004 009 804.2, DE-A 10 2004 009 805.0 or DE-A 10 2004 009 803.4.

Suitable W-containing and Re-free catalysts comprise preferably at least 3% by weight of W, at least partly in oxidic form, on a support selected from the group of alumina, aluminosilicates, zeolites or, preferably, $SiO_2$. The catalysts preferably have a surface area of at least 50 m²/g and a pore volume of at least 0.3 ml/g. The activity or isomerization activity may be improved by suitable dopants, for example alkali metal and alkaline earth metal compounds, $TiO_2$, $ZrO_2$, $HfO_2$, or compounds or elements from the group of Ag, Sb, Mn, W, Mo, Zn, Si. If a further increase in the 1-butene content is desired in the metathesis, it is also possible to mix with the W catalyst an isomerization catalyst, for example an alkaline earth metal oxide. This leads in the metathesis to the generation, in addition to propene, also of an additional amount of 1-butene which can in turn be fed to process stage b after distillative removal and increases the capacity here.

It is known to those skilled in the art that all types of metathesis catalysts regularly have to be regenerated oxidatively. To this end, either a construction with fixed beds and at least two reactors is selected, of which at least one reactor is always in regeneration mode, or a moving bed process may alternatively be practiced, in which deactivated catalyst is discharged and regenerated externally.

Especially in the case of the use of a rhenium catalyst, a useful embodiment is that of reactive distillation, in which the metathesis catalyst is placed directly within the distillation column. This embodiment is very suitable in particular in the presence of large amounts of 1-butene in the starting stream. In this case, unconverted ethylene, propene and 1-butene are taken overhead; the heavier olefins remain together with the catalyst in the bottom. If appropriate, discharge of inerts, for instance butanes, has to be ensured. This specific type of reaction allows the conversion of 2-butene to propene without the 1-butene content being altered.

The propene-containing hydrocarbon stream formed in the metathesis stage is worked up preferably by means of distillation. The distillative separation may be effected in a plurality of distillation stages connected in series or the propene-containing hydrocarbon stream formed in the metathesis stage may be fed at any point into the separation apparatus which splits the hydrocarbon mixture formed in the steam-cracker into individual fractions.

If a polymer is to be prepared in a subsequent step from the propene, the propene is purified further by customary methods such that it corresponds to the polymer-grade specification. According to this, the following upper limits apply for impurities:

| | |
|---|---|
| Propylene | >99.5% by weight |
| Propane | <5000 ppm by weight |
| Methane | <200 ppm by weight |
| Ethane | <300 ppm by weight |
| Ethylene | <30 ppm by weight |

EXAMPLES

The examples which follow, which are based on model calculations, are intended to illustrate arrangements for the utilization of $C_4$ streams. The components shown hereinbelow in dashed lines in the block schemes are in each case stages which are optional in principle. Some of these are also not used in the specific, accompanying text example.

Example 1

Example 1 is Illustrated Further by Scheme 1

From 400 000 tpa (metric tons per annum) of a crude $C_4$ stream from a naphtha cracker, approx. 75 000 tpa of 1,3-butadiene are removed by a butadiene extraction. After the selective hydrogenation, the remaining 325 000 tpa have the following composition: 30.8% isobutene, 30.8% 1-butene, 30.8% 2-butenes, 80 ppm of 1,3-butadiene, remainder butanes. This feed is fed to a stage for the selective hydroformylation of 1-butene. The 1-butene conversion is 90%; a total of 3% each of the 1-butene are converted in this process to 2-butene and butane respectively. Nearly 130 000 tpa of valeraldehyde are produced. The remaining $C_4$ stream (approx. 240 000 tpa) consists of 41.6% isobutene, 4.2% 1-butene, 42.7% 2-butenes, 100 ppm of 1,3-butadiene and remainder butanes. This feed is sent initially through a 13× molecular sieve for the removal of oxygenate traces and a total of 51 350 tpa of ethylene are subsequently fed to the metathesis stage. The metathesis runs in the gas phase over a fixed bed catalyst, 10% by weight of $WO_3$ on an $SiO_2$ support. The temperature is controlled to balance the advancing loss of activity and is 220° C. at the start of run and 400° C. at the end of run. When the end temperature has been attained after approx. 2 to 3 weeks, the catalyst is regenerated oxidatively at temperatures of approx. 550° C. In this time, a second, parallel reactor (A/B mode) takes over the production. At an average equilibrium conversion of approx. 55%, nearly 85 000 tpa of propene are produced. The stream formed in the metathesis stage is worked up by distillation, either in a separate distillation unit or it is fed for this purpose to the distillation unit which is attached downstream of a steamcracker. In the case of separate distillative workup, the stream is separated into at least 4 different fractions (see scheme): a) a fraction comprising mainly ethylene (fraction a), b) a fraction comprising mainly propene (fraction b), c) a fraction comprising $C_4$, $C_5$ and $C_6$ olefins, the $C_4$ olefins being mainly 2-butene, and d) a fraction comprising mainly low-boiling $C_4$ hydrocarbons (fraction d). Fraction a and c may subsequently be recycled back into the metathesis stage (alternatively: cracker). Fraction ($C_4$ content without taking the streams into account): c+d (184 000 tpa) is recycled to the cracker for reprocessing.

Example 2

Example 2 is Further Illustrated by Scheme 2

From 400 000 tpa of a crude $C_4$ stream from a naphtha cracker, approx. 100 000 tpa of 1,3-butadiene are removed by a butadiene extraction. After the selected hydrogenation, the remaining 300 000 tpa have the following composition: 36.7% isobutene, 26.7% 1-butene, 28.4% 2-butenes, 90 ppm of 1,3-butadiene, remainder butanes. This feed is fed to a stage for the selective hydroformylation of 1-butene. The 1-butene conversion is 85%; a total of in each case 4% of the 1-butene are converted in the process to 2-butene and butane respectively. Approx. 96 000 tpa of valeraldehyde are produced. The remaining $C_4$ stream (approx. 237 000 tpa) consists of 46.3% isobutene, 5.1% 1-butene, 38.1% 2-butenes, 110 ppm of 1,3-butadiene and remainder butanes. In a stage for the selective formation of polyisobutene, the isobutene is depleted to 5%. The acidic catalyst used is $BF_3$. Approx. 98 000 tpa of polyisobutene are obtained; the residual stream (approx. 134 000 tpa) consists of 5% isobutene, 8.9% 1-butene, 67.4% 2-butene, 190 ppm of 1,3-butadiene, remainder butanes.

This feed is initially also passed through a selective hydrogenation stage for the reduction of the 1,3-butadiene content to 80 ppm. The 1- to 2-butene content is not changed any further in this stage. Subsequently, a 13× molecular sieve removes oxygenate traces. The $C_4$ feed is subsequently fed to the metathesis stage together with approx. 45 000 tpa of ethylene. The metathesis runs in the liquid phase over a fixed bed catalyst, 10% by weight of $Re_2O_7$ on a gamma-alumina support. The temperature is controlled to balance the progressing loss of activity and is 35° C. at the start of run and 110° C. at the end of run. When the end temperature has been attained after approx. 1 week, the catalyst is regenerated oxidatively at temperatures of approx. 550° C. In this time, a second, parallel reactor (A/B mode) takes over the production. At an average equilibrium conversion of approx. 63%, around 64 000 tpa of propene are produced. The stream formed in the metathesis stage is worked up as described in scheme 1. The amount of the ($C_4$ content) fractions c+d is approx. 91 000 tpa.

Example 3

Example 3 is Further Illustrated by Scheme 3

375 000 tpa of a crude $C_4$ stream from a naphtha cracker are fed completely to a selective hydrogenation. Afterward, the stream has the following composition: 33.3% isobutene, 24% 1-butene, 40% 2-butenes, 100 ppm of 1,3-butadiene, remainder butanes. This feed is fed to a stage for the selective hydroformylation of 1-butene. The 1-butene conversion is 90%; a total of in each case 3.5% of the 1-butene are converted in the process to 2-butene and butane respectively. Around 115 000 tpa of valeraldehyde are produced. The remaining $C_4$ stream (nearly 300 000 tpa) consists of 41.7% isobutene, 3% 1-butene, 50.9% 2-butenes, 120 ppm of 1,3-butadiene and remainder butanes. This feed is split distillatively: the top product (136 000 tpa) consists of 80.5% isobutene, 5.8% 1-butene, 9.5% 2-butenes, 110 ppm of 1,3-butadiene, remainder butanes. The bottom product (163 000 tpa) consists of 9.3% isobutene, 0.7% 1-butene, 85.5% 2-butenes, 10 ppm of 1,3-butadiene, remainder butanes. The bottom product is sent initially through a 13× molecular sieve to remove oxygenate traces and a total of 70 000 tpa of ethylene are subsequently fed to the metathesis stage. The metathesis runs in the liquid phase over a fixed bed catalyst, 10% by weight of $Re_2O_7$ on an $Al_2O_3$ support. The temperature is controlled to balance the advancing loss of activity and is 40° C. at the start of run and 120° C. at the end of run. When the end temperature has been attained after approx. 6 days, the catalyst is regenerated oxidatively at temperatures of approx.

-continued

| | |
|---|---|
| Acetylene | <1 ppm by weight |
| Water | <10 ppm by weight |

550° C. In this time, a second, parallel reactor (A/B mode) takes over the production. At an average equilibrium conversion of approx. 63%, nearly 133 000 tpa of propene are produced. The stream formed in the metathesis stage is worked up as described in scheme 1. The amount of fraction ($C_4$ fraction) c+d is 75 000 tpa.

What is claimed is:

1. A process comprising:
   (a) providing a feedstream, the feedstream comprising butane, 1-butene, 2-butene and 1,3-butadiene, the 1,3-butadiene present in the feedstream in an amount up to 1000 ppm;
   (b) contacting the feedstream with hydrogen and carbon monoxide in the presence of a hydroformylation catalyst to form a 2-butene-rich butane stream and a $C_5$ aldehyde;
   (c) separating the 2-butene-rich butane stream and the $C_5$ aldehyde; and
   (d) contacting the 2-butene-rich butane stream with ethene in the presence of a metathesis catalyst to form a propene-containing hydrocarbon stream.

2. The process according to claim 1, wherein the feedstream is prepared by a process comprising: (i) cracking a hydrocarbon-containing stream to form an olefin mixture stream, wherein the olefin mixture stream comprises butane, 1-butene, 2-butene and 1,3-butadiene, the 1,3-butadiene present in an amount greater than 1000 ppm; and (ii) reducing the 1,3-butadiene content in the olefin mixture stream to less than 1000 ppm by subjecting the olefin mixture stream to a treatment selected from the group consisting of selective hydrogenation, extractive distillation, and combinations thereof.

3. The process according to claim 1, wherein the feedstream is prepared by a process comprising: (i) providing a hydrocarbon stream comprising butane; (ii) dehydrogenating and purifying the hydrocarbon stream to form an olefin mixture stream, wherein the olefin mixture stream comprises butane, 1-butene, 2-butene and 1,3-butadiene, the 1,3-butadiene present in an amount greater than 1000 ppm; and (iii) reducing the 1,3-butadiene content in the olefin mixture stream to less than 1000 ppm by subjecting the olefin mixture stream to a treatment selected from the group consisting of selective hydrogenation, extractive distillation, and combinations thereof.

4. The process according to claim 2, wherein the 1,3-butadiene is present in the olefin mixture stream in an amount of 5% by weight or more, and reducing the 1,3-butadiene content in the olefin mixture stream to less than 1000 ppm comprises extractive distillation to a 1,3-butadiene content of greater than 1000 ppm up to 5% by weight, and subsequent selective hydrogenation to a 1,3-butadiene content of 1000 ppm or less.

5. The process according to claim 3, wherein the 1,3-butadiene is present in the olefin mixture stream in an amount of 5% by weight or more, and reducing the 1,3-butadiene content in the olefin mixture stream to less than 1000 ppm comprises extractive distillation to a 1,3-butadiene content of greater than 1000 ppm up to 5% by weight, and subsequent selective hydrogenation to a 1,3-butadiene content of 1000 ppm or less.

6. The process according to claim 1, further comprising passing the 2-butene-rich butane stream through an absorbent bed comprising an absorbent selected from the group consisting of molecular sieves, aluminosilicates, alumina and combinations thereof.

7. The process according to claim 1, wherein 1-butene and 2-butene are present in the feedstream in a ratio of 3:1 to 1:3.

8. The process according to claim 1, wherein 1-butene and 2-butene are present in the 2-butene-rich butane stream in a ratio of 1:3 to 1:60.

9. The process according to claim 1, wherein the feedstream comprises butane in an amount of 2 to 50% by weight, 1-butene in an amount of 20 to 60% by weight, 2-butene in an amount of 15 to 80% weight, 1,3-butadiene in an amount of 20 to 1000 ppm, and up to 50% by weight of isobutene.

10. The process according to claim 7, wherein the feedstream comprises butane in an amount of 2 to 50% by weight, 1-butene in an amount of 20 to 60% by weight, 2-butene in an amount of 15 to 80% weight, 1,3-butadiene in an amount of 20 to 1000 ppm, and up to 50% by weight of isobutene.

11. The process according to claim 1, wherein the 2-butene-rich butane stream comprises butane in an amount of 3 to 70% by weight, 1-butene in an amount of 0 to 10% by weight, 2-butene in an amount of 22 to 90% weight, 1,3-butadiene in an amount of 20 to 1000 ppm, and up to 65% by weight of isobutene.

12. The process according to claim 8, wherein the 2-butene-rich butane stream comprises butane in an amount of 3 to 70% by weight, 1-butene in an amount of 0 to 10% by weight, 2-butene in an amount of 22 to 90% weight, 1,3-butadiene in an amount of 20 to 1000 ppm, and up to 65% by weight of isobutene.

13. The process according to claim 1, wherein the propene-containing hydrocarbon stream further comprises one or more olefins having 5 to 6 carbon atoms, and wherein the one or more olefins are separated from the propene-containing hydrocarbon stream and recycled to the reaction of the 2-butene-rich butane stream with the ethene such that the molar ratio of unrecycled one or more olefins to propene in the propene-containing hydrocarbon stream is 0.2:1 or less.

14. The process according to claim 1, wherein the feedstream comprises an amount of isobutene, and wherein the amount of isobutene is reduced by at least 40% during the process.

15. The process according to claim 14, wherein reducing the isobutene content comprises contacting the 2-butene-rich butane stream with an isobutene polymerization catalyst to form polyisobutene, and removing the polyisobutene.

16. The process according to claim 14, wherein reducing the isobutene content comprises contacting one or both of the feedstream and the 2-butene-rich butane stream with an alkyl alcohol and a catalyst to form an alkyl t-butyl ether, and removing the alkyl t-butyl ether.

17. The process according to claim 14, wherein reducing the isobutene content comprises distillation.

18. The process according to claim 1, further comprising removing propene from the propene-containing hydrocarbon stream by distillation.

19. The process according to claim 2, further comprising removing propene from the propene-containing hydrocarbon stream by distillation.

20. The process according to claim 1, further comprising removing propene from the propene-containing hydrocarbon stream by distillation.

* * * * *